United States Patent
Leventhal et al.

(10) Patent No.: US 9,994,817 B2
(45) Date of Patent: Jun. 12, 2018

(54) USE OF LIGANDS FOR THE PROGRAMMED CELL DEATH RECEPTOR CONJUGATED TO SOLID SUPPORTS FOR CULTIVATING HUMAN REGULATORY T CELLS

(71) Applicant: Northwestern University, Evanston, IL (US)

(72) Inventors: Joseph R. Leventhal, Chicago, IL (US); James M. Mathew, Arlington Heights, IL (US); Lorenzo Gallon, Chicago, IL (US); M. Javeed Ansari, Lombard, IL (US)

(73) Assignee: Northwestern University, Evanston, IL (US)

( * ) Notice: Subject to any disclaimer, the term of this patent is extended or adjusted under 35 U.S.C. 154(b) by 280 days.

(21) Appl. No.: 14/820,795

(22) Filed: Aug. 7, 2015

(65) Prior Publication Data

US 2016/0040127 A1 Feb. 11, 2016

Related U.S. Application Data

(60) Provisional application No. 62/034,555, filed on Aug. 7, 2014.

(51) Int. Cl.
| | |
|---|---|
| C12N 5/02 | (2006.01) |
| A61K 35/14 | (2015.01) |
| C12N 5/0783 | (2010.01) |
| A61K 35/17 | (2015.01) |

(52) U.S. Cl.
CPC ............ C12N 5/0637 (2013.01); *A61K 35/17* (2013.01); *C12N 2501/15* (2013.01); *C12N 2501/2302* (2013.01); *C12N 2531/00* (2013.01)

(58) Field of Classification Search
None
See application file for complete search history.

(56) References Cited

U.S. PATENT DOCUMENTS

| 2012/0076805 A1* | 3/2012 | Sharpe | C12N 5/0636 424/184.1 |
|---|---|---|---|
| 2014/0341933 A1* | 11/2014 | Riley | C12N 5/0637 424/184.1 |

FOREIGN PATENT DOCUMENTS

WO 2009155477 12/2009

OTHER PUBLICATIONS

User Manual "Dynabeads® Regulatory CD4+CD25+ T Cell Kit," Catalog No. 11363D. Invitrogen, 2012, 2 pages.*
Francisco LM, Salinas VH, Brown KE, et al; PD-L1 Regulates the Development, Maintenance, and Function of Induced Regulatory T Cells. JEM 2009; 206:3015-3029.
Francisco LM, Sage PT, and Sharpe AH; The PD-1 Pathway in Tolerance and Autoimmunity. Immunol Rev 201 236:219-242.
Rabe et al., "*Staphylococcus aureus* convert neonatal conventional CD4+ T cells into FOXP3+ CD23+ CD127 low T cells via the PD-1/PD-L1 axis," Immunology, 2013, 141(3):467-481.
Riella LV, Paterson AM, Sharpe AH, Chandraker; A Role of the PD-1 Pathway in the Immune Response AJT 2012 12:2575-2587.
International Search Report for PCT/US2015/044174 dated Nov. 12, 2015.
Written Opinion for PCT/US2015/044174 dated Nov. 12, 2015.
International Preliminary Report on Patentability for PCT/US2015/044174 dated Feb. 16, 2017.

* cited by examiner

*Primary Examiner* — Ilia I Ouspenski
(74) *Attorney, Agent, or Firm* — Andrus Intellectual Property Law, LLP

(57) ABSTRACT

Disclosed are methods for isolating, cultivating, and/or cells including regulatory T cells (Tregs). The methods typically include cultivating cells including Tregs in a culture media comprising a ligand for programmed cell death receptor (PD-1) conjugated to a solid support. Suitable ligands may include PD-L1 and suitable solid supports may include magnetic or paramagnetic beads where the methods further include removing the PD-L1/bead conjugates after the Tregs have been isolated, cultured, and/or expanded.

20 Claims, 11 Drawing Sheets

SEQUENCE LISTING

```
<160> NUMBER OF SEQ ID NOS: 3

<210> SEQ ID NO 1
<211> LENGTH: 290
<212> TYPE: PRT
<213> ORGANISM: Homo sapien

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175
```

```
Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                    245                 250                 255

Phe Ile Phe Arg Leu Arg Lys Gly Arg Met Met Asp Val Lys Lys Cys
                    260                 265                 270

Gly Ile Gln Asp Thr Asn Ser Lys Lys Gln Ser Asp Thr His Leu Glu
                    275                 280                 285

Glu Thr
    290

<210> SEQ ID NO 2
<211> LENGTH: 176
<212> TYPE: PRT
<213> ORGANISM: Homo sapien

<400> SEQUENCE: 2

Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
                20                  25                  30

Val Thr Ser Glu His Glu Leu Thr Cys Gln Ala Glu Gly Tyr Pro Lys
            35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Thr Asn Glu Ile Phe Tyr Cys Thr
                85                  90                  95

Phe Arg Arg Leu Asp Pro Glu Glu Asn His Thr Ala Glu Leu Val Ile
            100                 105                 110

Pro Glu Leu Pro Leu Ala His Pro Pro Asn Glu Arg Thr His Leu Val
        115                 120                 125

Ile Leu Gly Ala Ile Leu Leu Cys Leu Gly Val Ala Leu Thr Phe Ile
    130                 135                 140

Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175

<210> SEQ ID NO 3
<211> LENGTH: 273
<212> TYPE: PRT
<213> ORGANISM: Homo sapien

<400> SEQUENCE: 3

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30
```

-continued

```
Glu His Gly Ser Asn Val Thr Leu Glu Cys Asn Phe Asp Thr Gly Ser
        35                  40                  45
His Val Asn Leu Gly Ala Ile Thr Ala Ser Leu Gln Lys Val Glu Asn
    50                  55                  60
Asp Thr Ser Pro His Arg Glu Arg Ala Thr Leu Leu Glu Glu Gln Leu
65                  70                  75                  80
Pro Leu Gly Lys Ala Ser Phe His Ile Pro Gln Val Gln Val Arg Asp
                85                  90                  95
Glu Gly Gln Tyr Gln Cys Ile Ile Ile Tyr Gly Val Ala Trp Asp Tyr
                100                 105                 110
Lys Tyr Leu Thr Leu Lys Val Lys Ala Ser Tyr Arg Lys Ile Asn Thr
            115                 120                 125
His Ile Leu Lys Val Pro Glu Thr Asp Glu Val Glu Leu Thr Cys Gln
        130                 135                 140
Ala Thr Gly Tyr Pro Leu Ala Glu Val Ser Trp Pro Asn Val Ser Val
145                 150                 155                 160
Pro Ala Asn Thr Ser His Ser Arg Thr Pro Glu Gly Leu Tyr Gln Val
                165                 170                 175
Thr Ser Val Leu Arg Leu Lys Pro Pro Pro Gly Arg Asn Phe Ser Cys
            180                 185                 190
Val Phe Trp Asn Thr His Val Arg Glu Leu Thr Leu Ala Ser Ile Asp
        195                 200                 205
Leu Gln Ser Gln Met Glu Pro Arg Thr His Pro Thr Trp Leu Leu His
    210                 215                 220
Ile Phe Ile Pro Ser Cys Ile Ile Ala Phe Ile Phe Ile Ala Thr Val
225                 230                 235                 240
Ile Ala Leu Arg Lys Gln Leu Cys Gln Lys Leu Tyr Ser Ser Lys Asp
                245                 250                 255
Thr Thr Lys Arg Pro Val Thr Thr Thr Lys Arg Glu Val Asn Ser Ala
                260                 265                 270
Ile
```

USE OF LIGANDS FOR THE PROGRAMMED CELL DEATH RECEPTOR CONJUGATED TO SOLID SUPPORTS FOR CULTIVATING HUMAN REGULATORY T CELLS

CROSS-REFERENCED TO RELATED PATENT APPLICATIONS

The present patent application claims the benefit of priority under 35 U.S.C. 119(e) to U.S. Provisional Patent Application No. 62/034,555, filed on Aug. 7, 2014, the content of which is incorporated herein by reference in its entirety.

BACKGROUND

The field of the invention relates to regulatory T cells (Tregs). In particular, the field of the invention relates to methods for isolating, cultivating, and/or expanding Tregs.

Regulatory T cells (Tregs) are critical regulators of the immune system. Efforts are underway to develop strategies to isolate and expand naturally occurring human Tregs (nTregs) to use as cellular therapies to help control autoimmune disease, graft versus host disease, and organ transplant rejection. nTregs are few in number in the blood and need to be expanded in number significantly to be used as a therapy.

Human B7 homolog (B7-H1), also called programmed cell death ligand 1 (PD-L1) is a member of a growing family of immune proteins that provide signals for both stimulating and inhibiting T cell activation (1-3). Importantly, the interaction of PD-L1 with its ligand PD-1 results in inhibition of T cell receptor (TCR) mediated proliferation and cytokine production predominantly in effector T cell populations. Published work has shown the ability of the PD-L1 to induce naïve T cells to become regulatory T cells (3). As detailed herein, the inventors have used programmed death-ligand 1 (PD-L1) conjugated to paramagnetic beads to promote the expansion of human nTregs that are highly suppressive and potentially effective for the treatment of inflammation and rejection. This approach is applicable to the expansion of both antigen specific as well as antigen nonspecific naturally-occurring Tregs.

SUMMARY

Disclosed are methods for isolating, cultivating, and/or expanding cells including regulatory T cells (Tregs). The methods typically include cultivating cells including Tregs in a culture media comprising a ligand for the programmed cell death receptor (PD-1) conjugated to a solid support. Suitable ligands may include programmed cell death ligand 1 (PD-L1) conjugated to a solid support. Suitable solid supports for PD-L1 may include magnetic or paramagnetic beads where the methods further include removing the PD-L1/bead conjugates from the culture media after the Tregs have been isolated, cultured, and/or expanded.

The cells isolated, cultivated and/or expanded by the disclosed methods preferably have a phenotype that is characterized as $CD4^+$, $CD25^+$, $CD127^{low}$, $Foxp3^+$. In some embodiments of the disclosed methods, a population of cells is isolated, cultivated and/or expanded where greater than about 80%, 90%, 95%, 96%, 97%, or 98% of the cells of the population have a phenotype of $CD4^+$, $CD25^+$, $CD127^{low}$ and/or greater than about 40%, 50%, 60%, 70%, 80%, or 90% of the cells of the population have a phenotype of $Foxp3^+$.

The disclosed methods may include isolating Tregs from peripheral blood mononuclear cells (PBMCs), for example, prior to cultivating and/or expanding the Tregs in the presently disclosed methods. In some embodiments, the Tregs may be isolated from the PBMCs by removing cells that are $CD8^+$ and $CD19^+$ from the PMBCs and by selecting for cells that are $CD25^+$.

In the disclosed methods, Tregs are cultivated in a culture media comprising a ligand for PD-1 conjugated to a solid support. PD-L1 is one suitable ligand for the programmed cell death receptor (PD). In some embodiments, the methods further may comprise cultivating the Tregs in a culture media comprising another ligand for PD-1 (e.g., PD-L2) or another ligand for another T cell receptor.

In some embodiments, the methods further may comprise cultivating the Tregs in a culture media comprising an antibody against PD-1 or an antibody against another T cell receptor, for example where the antibody is conjugated to a solid support. Used as such, an antibody may function as an agonist for the cell receptor, or alternatively the antibody may function as an antagonist or inhibitor for the cell receptor.

The culture media utilized in the disclosed methods comprises a ligand for PD-1 conjugated to a solid support and optionally may include additional agents for cultivating Tregs. Additional agents may include, but are not limited to, cytokines, growth factors, and agents that inhibit activation of effector T cells and/or B cells.

Also disclosed are Tregs obtained by the disclosed methods and methods for using the Tregs thus obtained for treating and preventing diseases, disorders, and conditions. In some embodiments, the Tregs obtained by the disclosed methods may be formulated as a pharmaceutical agent. In further embodiments, the pharmaceutical agent comprising the Tregs may be administered to a patient in order to treat or prevent a disease, disorder, or condition that is treated or prevented by administering Tregs.

Also disclosed are culture media for Tregs. The culture media typically include a ligand for PD-1 conjugated to magnetic or paramagnetic beads. Preferably, the culture media include additional components for cultivating and expanding Tregs from a population of T cells.

DETAILED DESCRIPTION

Figure 1:
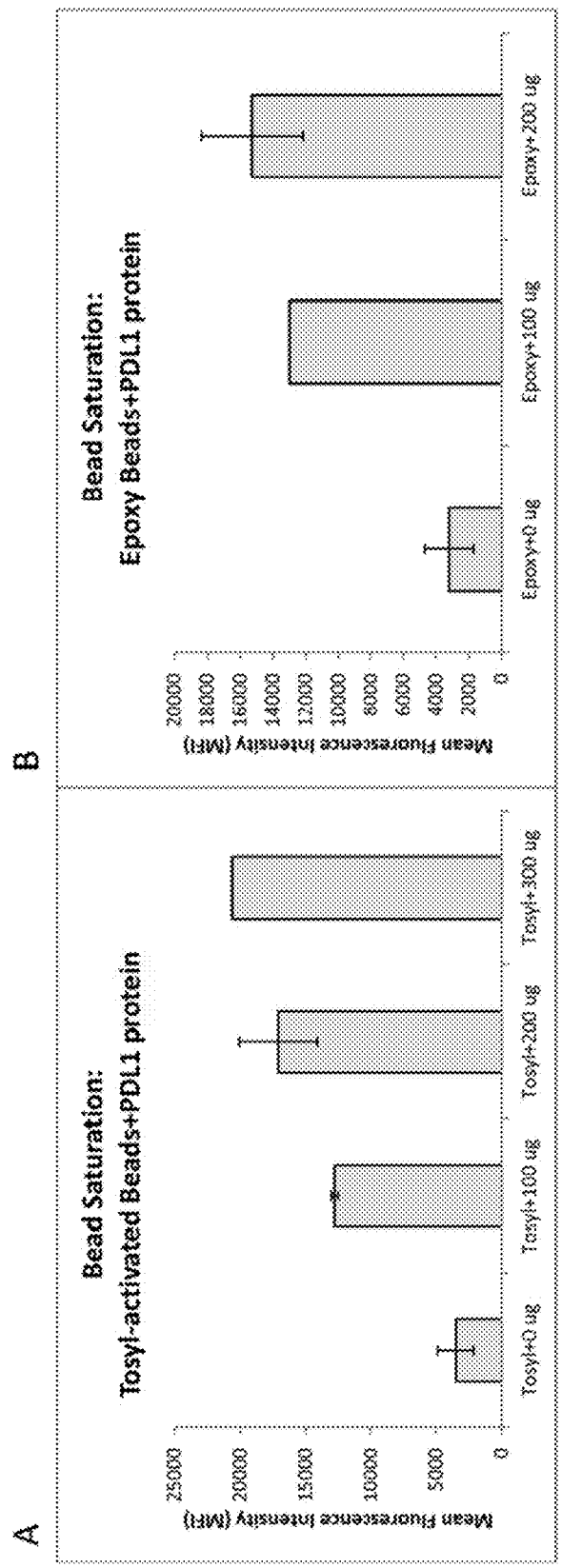
FIG. 1. Bead saturation study. A. Tosyl-activated beads+PD-L1 protein. B. Epoxy beads+PD-L1 protein.

The present invention is described herein using several definitions, as set forth below and throughout the application.

As used in this specification and the claims, the singular forms "a," "an," and "the" include plural forms unless the content clearly dictates otherwise. For example, the term "a ligand for PD-1" should be interpreted to mean "one or more ligands for PD-1." As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

As used herein and as understood in the field of immunology, "regulatory T cells" or "Tregs," formerly known as "suppressor T cells," are a subpopulation of T cells which modulate the immune system, maintain tolerance to self-antigens, and prevent autoimmune disease. Tregs may be distinguished based on expression of cell surface markers where Tregs generally have the phenotype: CD4$^+$, CD25$^+$, CD127$^{low}$, Foxp3$^+$. In particular, Tregs that express CD4$^+$ and Foxp3$^+$ have been called "natural Tregs" or "nTregs" to distinguish them from "suppressor" T cell populations that are generated in vitro.

As used herein, the term "patient" may be used interchangeably with the term "subject" or "individual" and may include an "animal" and in particular a "mammal." Mammalian subjects may include humans and other non-human primates, domestic animals, farm animals, and companion animals such as dogs, cats, guinea pigs, rabbits, rats, mice, horses, cattle, cows, and the like.

A "patient in need thereof" is intended to include a patient having or at risk for developing a disease or condition that may be treated or prevented by administering Tregs to the patient. In particular, a "patient in need thereof" is intended to include a patient having or at risk for developing an autoimmune disease, a graft versus host disease, an organ transplant rejection, rheumatoid arthritis, an inflammatory bowel disease, diabetes (e.g., Type I diabetes), and a cell proliferative disease or disorder such as cancer.

Disclosed are methods for isolating, cultivating, and/or expanding cells including Tregs. The methods typically include cultivating cells including Tregs in a culture media comprising a ligand for PD-1 (e.g. PD-L1) conjugated to a solid support, such as magnetic or paramagnetic beads, where the methods further include removing the bead conjugates from the culture media after the Tregs have been isolated, cultured, and/or expanded.

Suitable PD-1 ligands may include programmed cell death ligand 1 (PD-L1), programmed cell death ligand 2 (PD-L2), or variants, mutants, or derivatives thereof. The amino acid sequences of PD-L1 isoform a is provided as SEQ ID NO:1; the amino acid sequence of PD-L1 isoform b is provided as SEQ ID NO:2; and the amino acid sequence of PD-L2 is provided as SEQ ID NO:3. Variants, mutants, and derivatives of SEQ ID NOs:1-3 are described as follows.

The terms "amino acid" and "amino acid sequence" refer to an oligopeptide, peptide, polypeptide, or protein sequence (which terms may be used interchangeably), or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

As utilized herein, a protein, polypeptide, and peptide refer to a molecule comprising a chain of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Tip or W), and tyrosine (Tyr or Y) residues. The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine.

The amino acid sequences contemplated herein may include conservative amino acid substitutions relative to a reference amino acid sequence. For example, a variant, mutant, or derivative polypeptide may include conservative amino acid substitutions relative to a reference polypeptide. "Conservative amino acid substitutions" are those substitutions that are predicted to interfere least with the properties of the reference polypeptide. In other words, conservative amino acid substitutions substantially conserve the structure and the function of the reference protein. The following Table provides a list of exemplary conservative amino acid substitutions.

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid sequence that results in the absence of one or more amino acid residues. A deletion removes at least 1, 2, 3, 4, 5, 10, 20, 50, 100, or 200 amino acids residues. A deletion may include an internal deletion or a terminal deletion (e.g., an N-terminal truncation or a C-terminal truncation of a reference polypeptide). A "variant," "mutant," or "derivative" of a reference polypeptide sequence may include a deletion relative to the reference polypeptide sequence.

The words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, or 200 amino acid residues. A "variant," "mutant," or "derivative" of a reference polypeptide sequence may include an insertion or addition relative to the reference polypeptide sequence.

A "fusion polypeptide" refers to a polypeptide, such as a ligand for PD-1 as contemplated herein, comprising at the N-terminus, the C-terminus, or at both termini of its amino acid sequence a heterologous amino acid sequence, for example, an Fc portion of an antibody that facilitates binding or conjugation of the fusion polypeptide to a solid support. A "variant," "mutant," or "derivative" of a reference polypeptide sequence may include a fusion polypeptide comprising the reference polypeptide fused to a heterologous polypeptide.

A "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full length polypeptide. A "variant," "mutant," or "derivative" of a reference polypeptide sequence may include a fragment of the reference polypeptide sequence.

"Homology" refers to sequence similarity or, interchangeably, sequence identity, between two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See. e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant," "mutant," or "derivative" of a particular polypeptide sequence may be defined as a polypeptide sequence having at least 20% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides.

A "variant," "mutant" or a "derivative" may have substantially the same functional activity as a reference polypeptide. For example, a variant, mutant, or derivative of a ligand for PD-1 may bind PD-1 and function as an agonist or and antagonist.

A protein, polypeptide, or peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a non-enzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

Also contemplated herein are peptidomimetics of the disclosed proteins, polypeptides, and peptides. As disclosed herein, a peptidomimetic is an equivalent of a protein, polypeptide, or peptide characterized as retaining the polarity, three dimensional size and functionality (bioactivity) of the protein, polypeptide, or peptide equivalent but where the protein, polypeptide, or peptide bonds have been replaced (e.g., by more stable linkages which are more resistant to enzymatic degradation by hydrolytic enzymes). Generally, the bond which replaces the amide bond conserves many of the properties of the amide bond (e.g., conformation, steric bulk, electrostatic character, and possibility for hydrogen bonding). A general discussion of prior art techniques for the design and synthesis of peptidomimetics is provided in "Drug Design and Development", Chapter 14, Krogsgaard, Larsen, Liljefors and Madsen (Eds) 1996, Horwood Acad. Pub, the contents of which are incorporated herein by reference in their entirety. Suitable amide bond substitutes include the following groups: N-alkylation (Schmidt, R. et. al., Int. J. Peptide Protein Res., 1995, 46, 47), retro-inverse amide (Chorev, M and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391), which all are incorporated herein by reference in their entireties. Contemplated herein are peptidomimetic equivalents of the disclosed ligands for PD-1, for example, conjugated to a solid support.

The solid support typically has a surface with functional groups that react with primary amino groups and/or sulfhydryl groups. As such, the functional groups may react with a protein comprising primary amino groups and/or sulfhydryl groups in order to conjugate the protein to the surface of the solid support. Suitable functional groups on the surface of the solid support may include, but are not limited to, epoxy groups and tosyl groups.

Suitable solid supports may include microscale or nanoscale beads. For example, suitable solid supports may include beads having an effective average diameter of 0.5-20 µm, (or beads having an effective average diameter of 0.5-15 µm, 0.5-10 µm).

The solid support may comprise any suitable solid material. Preferably, the solid support comprises polymeric material that is magnetic, paramagnetic, or superparamagnetic. Suitable polymeric material may include superparamagnetic polystyrene material.

Suitable solid support may comprise cell culture containers (e.g., dishes, microwells, roller bottles, and the like), for example where the surface of the container is coated and conjugated to a ligand for PD-1. Suitable ligands may include PD-L1.

In the disclosed methods, the culture media includes a suitable ratio of cells to the PD-1 ligand. For example, where PD-L1 is conjugated to beads and the beads are saturated with PD-L1, suitable ratios of cells:beads in the culture media may include approximately 1:1, 1:2, 1:4, 1:8, 1:16, 1:32 (and preferably the ratio of cells:beads is approximately 1:2).

The cells isolated, cultivated, and/or expanded by the disclosed methods preferably have a phenotype that is characterized as $CD4^+$, $CD25^+$, $CD127^{low}$, $Foxp3^+$. In some embodiments of the disclosed methods, a population of cells is isolated, cultivated, and/or expanded, where greater than about 80%, 90%, 95%, 96%%, 97%, or 98% of the cells of the population have a phenotype of $CD4^+$, $CD25^+$, $CD127^{low}$ (and preferably greater than 99% of the cells of the population have a phenotype of $CD4^+$, $CD25^+$, $CD127^{low}$, (and/or greater than about 40%, 50%, 60%, 70%, 80%, or 90% of the cells of the population have a phenotype of $Foxp3^+$ (and preferably greater than 95%, 96%, 97%, 98%, or 99% of the cells of the population have a phenotype of $Foxp3^+$).

The disclosed methods may include isolating Tregs from peripheral blood mononuclear cells (PBMCs), for example, prior to cultivating and/or expanding the Tregs in the presently disclosed methods. In some embodiments, the Tregs may be isolated from the PBMCs by removing cells that are $CD8^+$ and $CD19^+$ from the PMBCs and by selecting for cells that are $CD25^+$ (e.g., to obtain a population of cells where at least 80% or 90% of the cells of the population have the phenotype $CD8^{low}CD19^{low}CD25^+$, and preferably at least 95%, 96%, 97%, 98%, or 99% of the cells of the population have the phenotype $CD8^{low}CD19^{low}CD25^+$).

In the disclosed methods, Tregs are cultivated in a culture media comprising a ligand for PD-1 conjugated to a solid support. For example, PD-L1 is one suitable ligand for PD-1. Recombinant PD-L1 is available commercially in the form of a recombinant human B7-H1/PD-L1 Fc Chimera. (See R&D Systems, Catalog Number: 156-B7). As such, the recombinant human B7-H1/PD-L1 Fc Chimera may be referred to as a fusion protein as discussed herein. In some embodiments, the methods further may comprise cultivating the Tregs in a culture media comprising another ligand for the PD receptor (e.g., PD-L2) or another ligand for another T cell receptor.

In some embodiments, the methods further may comprise cultivating the Tregs in a culture media comprising an antibody against PD-1 or an antibody against another T cell receptor, for example where the antibody is conjugated to a solid support. Used as such, an antibody may function as an agonist for the cell receptor, or alternatively the antibody may function as an antagonist or inhibitor for the cell receptor. For example, the methods further may comprise cultivating the Tregs in a culture media comprising an antibody against CD3 conjugated to a solid support and/or cultivating the Tregs in a culture media comprising an antibody against CD28 conjugated to a solid support. Optionally, the methods may comprise cultivating the Tregs in a culture media comprising an antibody against CD3 and an antibody against CD28 both conjugated to the same solid support. In some specific embodiments of the disclosed methods the culture media for cultivating the Tregs may include a PD-L1 bead conjugate and an anti-CD3/anti-CD28/bead conjugate.

In the disclosed methods, the culture media comprises a ligand for PD-1 conjugated to a solid support (e.g., PD-L1 conjugated to a solid support) and optionally may include additional agents for cultivating Tregs. Additional agents may include, but are not limited to, cytokines, growth factors, and agents that inhibit activation of effector T cells and/or B cells. For example, in some embodiments of the disclosed methods, the culture media further comprises IL-2. In other embodiments of the disclosed methods, the culture media further comprises rapamycin. In further embodiments of the disclosed methods, the culture media further comprises TGF-beta.

Also disclosed are Tregs obtained by the disclosed methods and methods for using the Tregs thus obtained for treating and preventing diseases, disorders, and conditions. In some embodiments, the Tregs obtained by the disclosed methods may be formulated as a pharmaceutical agent. In further embodiments, the pharmaceutical agent comprising the Tregs may be administered to a patient in order to treat or prevent a disease, disorder, or condition that is treated or prevented by administering Tregs. Suitable diseases, disorders, and conditions that may be treated or prevented by administering Tregs obtained as disclosed herein include but are not limited to autoimmune diseases, graft-versus-host diseases, organ transplant rejections, rheumatoid arthritis, inflammatory bowel diseases, diabetes (e.g., Type I diabetes), and cell proliferative diseases (e.g., cancer).

Also disclosed are culture media for cultivating and/or expanding Tregs from a population of Tcells (e.g., from PMBCs). The culture media typically includes a ligand for PD-1 conjugated to magnetic or paramagnetic beads (e.g., PD-L1) conjugated to magnetic or paramagnetic beads). Optionally, the culture media further include an antibody against CD3 conjugated to a solid support and/or an antibody against CD28 conjugated to a solid support. Optionally, the culture media further include a cytokine, a growth factor, and/or an agent that inhibits activation and/or proliferation of effector T cells and/or B cells (e.g. rapamycin).

EXAMPLE

The following examples are illustrative and are not intended to limit the scope of the claimed subject matter.

Example 1—Human PD-L1 Conjugated Beads for the Ex Vivo Expansion of Naturally Occurring Regulatory T Cells Abstract The inventors have prepared PD-L1/paramagnetic beads using a human PD-L1-Fc chimeric protein, which is a recombinant disulfide linked homodimer derived from a mouse myeloma cell line. The terminal Ig-like Fc domain of this protein allows for the covalent attachment to beads used for the activation and expansion of nTregs. Following bead conjugation, the inventors determined a >98% efficiency of bead conjugation by flow cytometric analysis of the resulting bead product. Using the PD-L1 conjugated beads in combination with a robust T cell activation signal (CD3+/CD28+ activation for achieving polyclonal activation of T cells), the inventors cultivated and expanded nTregs from peripheral blood mononuclear cells (PBMCs) capable of mediating immune suppression. The population of cells exhibited a phenotype in which >98% of the cells were CD4$^+$, CD25$^+$, CD127$^{low}$, and >90% of the cells were Foxp3$^+$, indicative of a phenotypic nTreg population. The inventors demonstrated that the nTreg population thus cultivated and expanded as able to inhibit the proliferation of autologous effector T cells. The addition of expanded nTregs at a 1:1 ratio to effector T cells resulted in >80% inhibition of proliferation of autologous effector T cells. In summary, this data indicates that the inventors' human PD-L1 bead conjugate can be used to achieve a robust expansion of human nTregs, and that the expanded nTregs retain suppressive efficacy.

Development of PD-L1 Conjugated Beads

Figure 2:
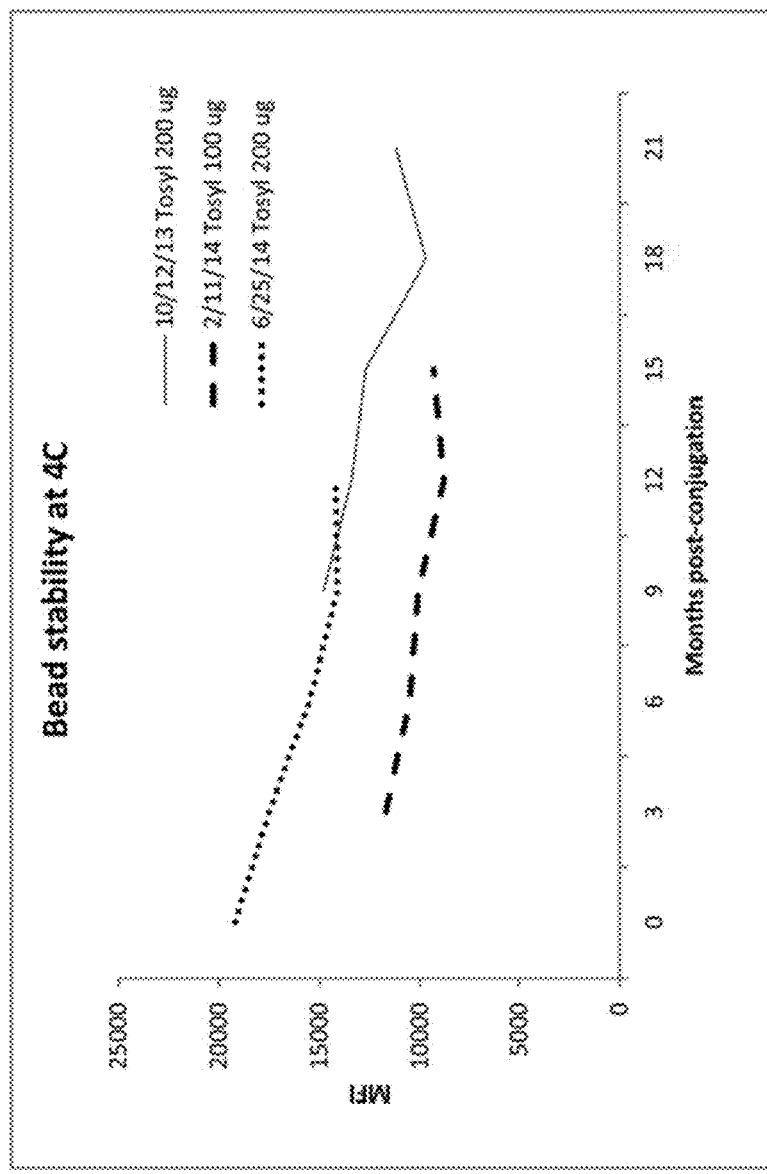
FIG. 2. Conjugated tosyl-activated bead stability at 4° C.

Recombinant human PD-1-Ig chimeric protein was purchased from R & D systems (Catalog Number 156-B7). This recombinant disulfide linked homodimer is derived from a mouse myeloma cell line. The terminal Ig like Fc domain of this protein allows for the covalent attachment to beads used for the activation and expansion of nTregs. M450 Tosyl-activated Dynabeads and M450 Epoxy Dynabeads were purchased from Invitrogen and used to covalently attach human PD-L1-Ig using manufacturer instructions. Following bead conjugation, the inventors determined a >98% efficiency of bead conjugation by flow cytometric analysis of the resulting bead product. By conjugating an equivalent of 200 μg protein per 1 mL of beads, the inventors observed near saturation levels and produced conjugated beads having a highly detectable signal with >98% conjugation efficiency. (See FIGS. 1A and B). To maintain protein stability and conjugation efficiency, the lyophilized PD-L1 protein stock was not subjected to multiple freeze-thaw events after re-suspension in PBS. Conjugated beads were relatively stable over time when kept at 4° C. at sterile conditions. The mean fluorescence intensity (MFI) was reduced at a stable pace over a span of 12 months, losing only about 30% of its intensity. The beads lose only a small fraction of intensity over the first 3 months. (See FIG. 2).

Figure 3:
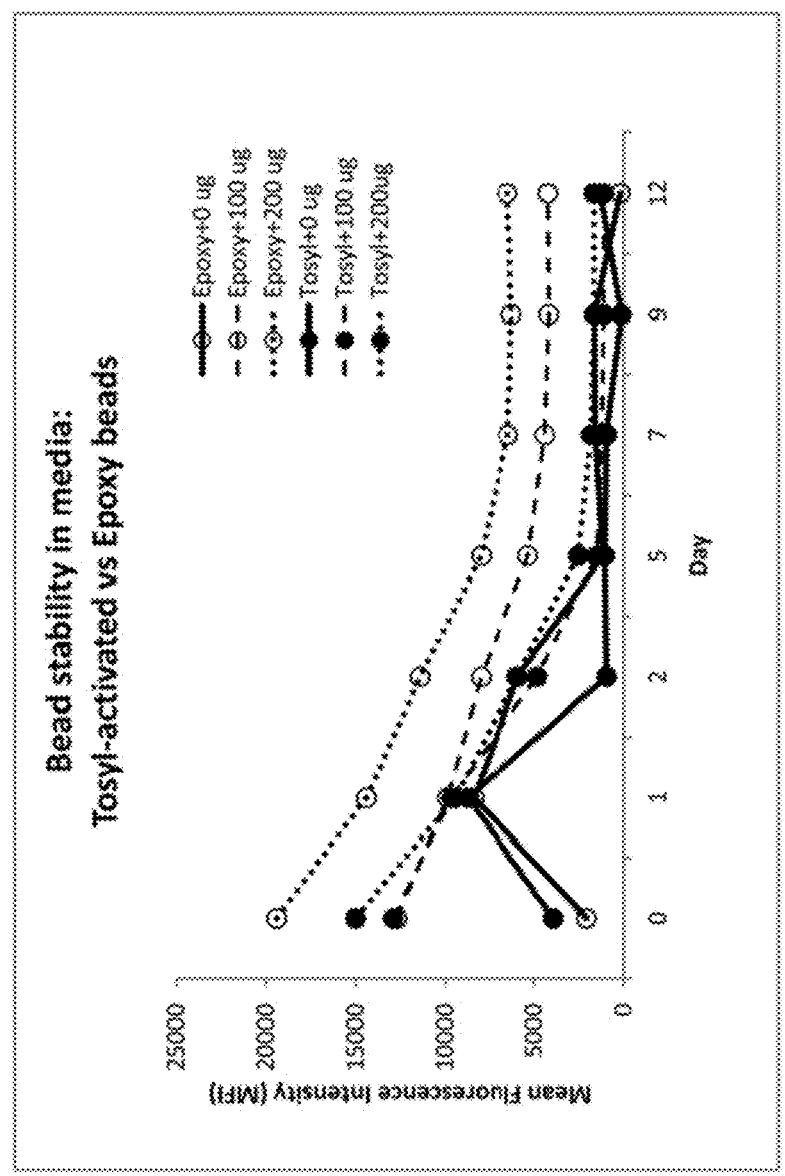
FIG. 3. Stability of PD-L1 when conjugated to epoxy beads versus tosyl-activated beads.
Figure 4:
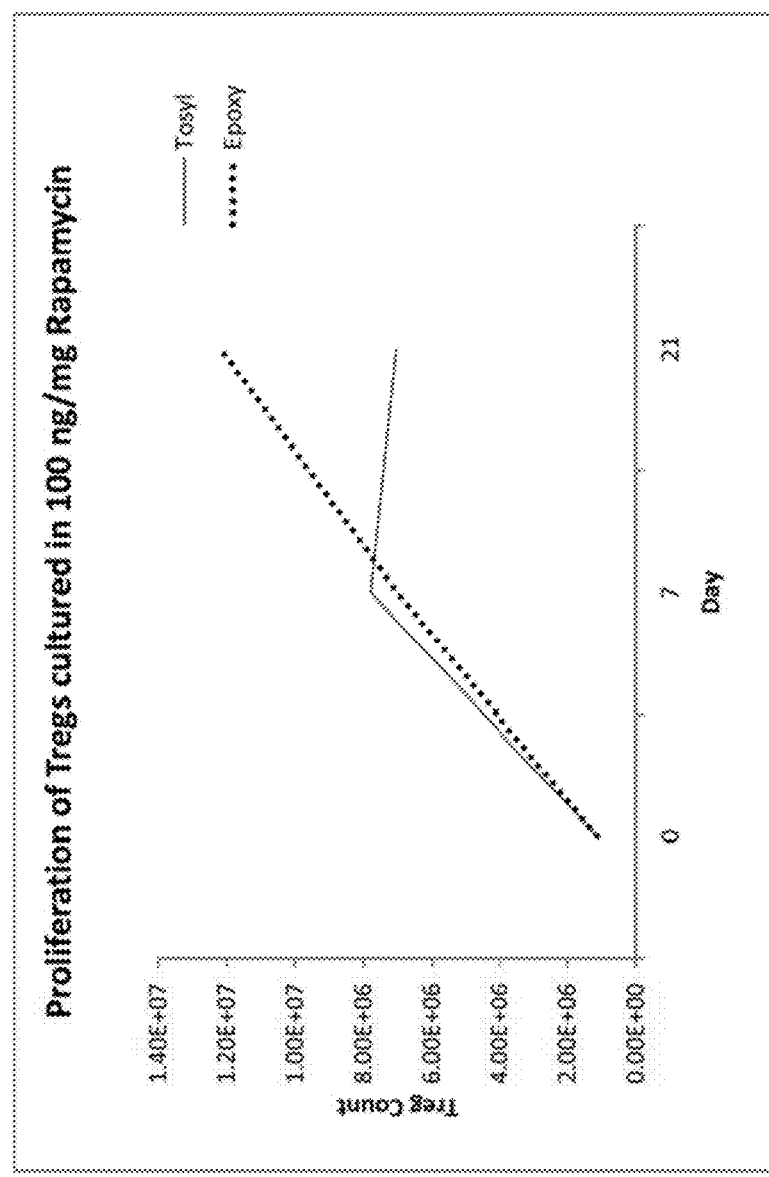
FIG. 4. Proliferation of Tregs cultured with PD-L1 conjugated epoxy beads versus PD-L1 conjugated tosyl-activated beads.

Stability of PD-L1 protein in culture medium was higher when conjugated to Epoxy Dynabeads in comparison to Tosyl-Activated Dynabeads. Stability of beads was determined by incubation in conditioned medium from sampled supernatant of Treg cultures. The results indicated that while Epoxy-conjugated PD-L1 beads retain 50% of bead intensity at day 5 of culture, the half-life of Tosyl-conjugated PD-L1 beads is only 1 day. (See FIG. 3). In addition, data from in vitro expansion of Tregs suggests that Tregs expand more robustly when treated with PD-L1 conjugated to Epoxy beads (see FIG. 4) than to Tosyl-Activated beads. This data is consistent with enhanced bead stability in culture medium. (See FIG. 3).

Use of PD-L1 Conjugated Beads for nTreg Expansion

In the inventors' initial experiments using the PD-L1 conjugated beads for nTreg expansion, the expanded population of human nTregs consistently exhibited a phenotype where >98% of the population of cells had a phenotype of CD4+, CD25+, >90% CD127 low, and >90% of the population of cells had a phenotype of Foxp3+. The ability of PD-L1/CD3-CD28 bead expanded nTregs to inhibit the proliferation of autologous effector T cells was also assessed. Expanded nTregs were added to a mixed lymphocyte reaction using autologous T effector cells as responders and a mismatched donor as stimulator. The resulting proliferation was determined through the incorporation of tritiated thymidine. The addition of expanded nTregs at a 1:1 ratio to effector Tcells resulted in >80% inhibition of proliferation of autologous effector T cells. In summary, this data indicates that the inventors' use of a human PD-1 bead conjugate can be used to achieve the robust expansion of human nTregs, and that the expanded nTregs retain suppressive efficacy.

Figure 5:
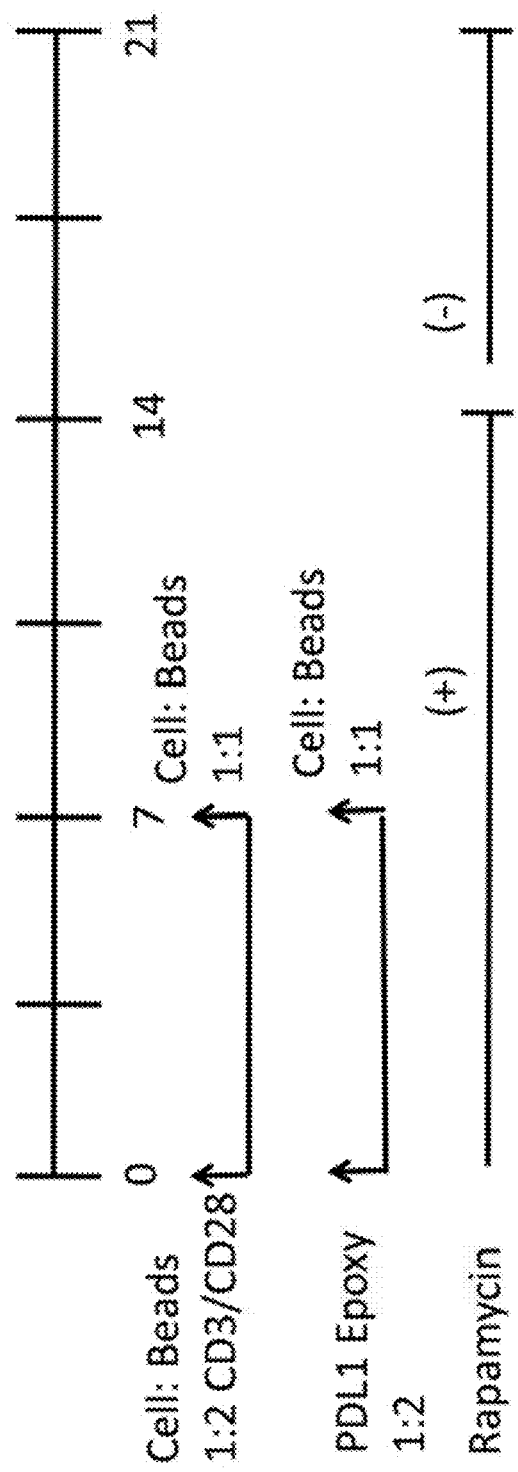
FIG. 5. Exemplary expansion protocol for Tregs.
Figure 6:
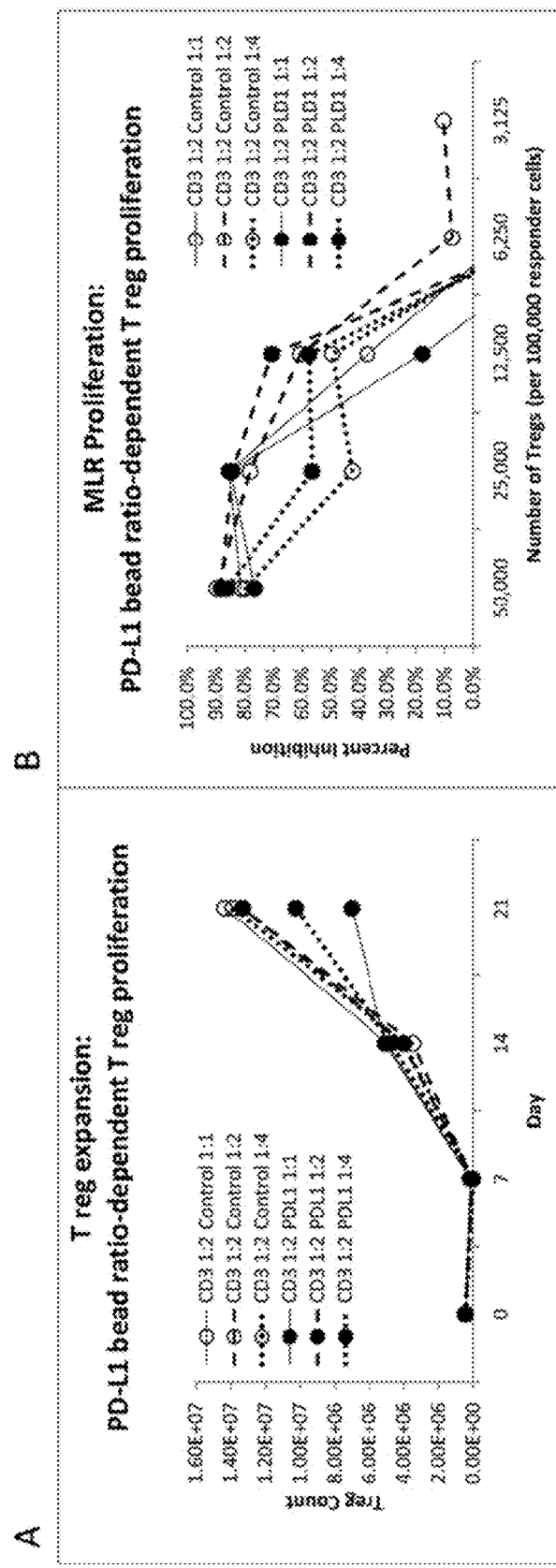
FIG. 6. A. Treg expansion in 1:2 cell to bead ratio of PD-L1-Epoxy bead with 1:2 cell to bead ratio of CD3/CD28 beads, cultured in 100 ng/ml Rapamycin. B. MLR inhibition potential of Tregs cultured in 1:1 vs 1:2 vs 1:4 cell to PDL1 bead ratio.
Figure 7:
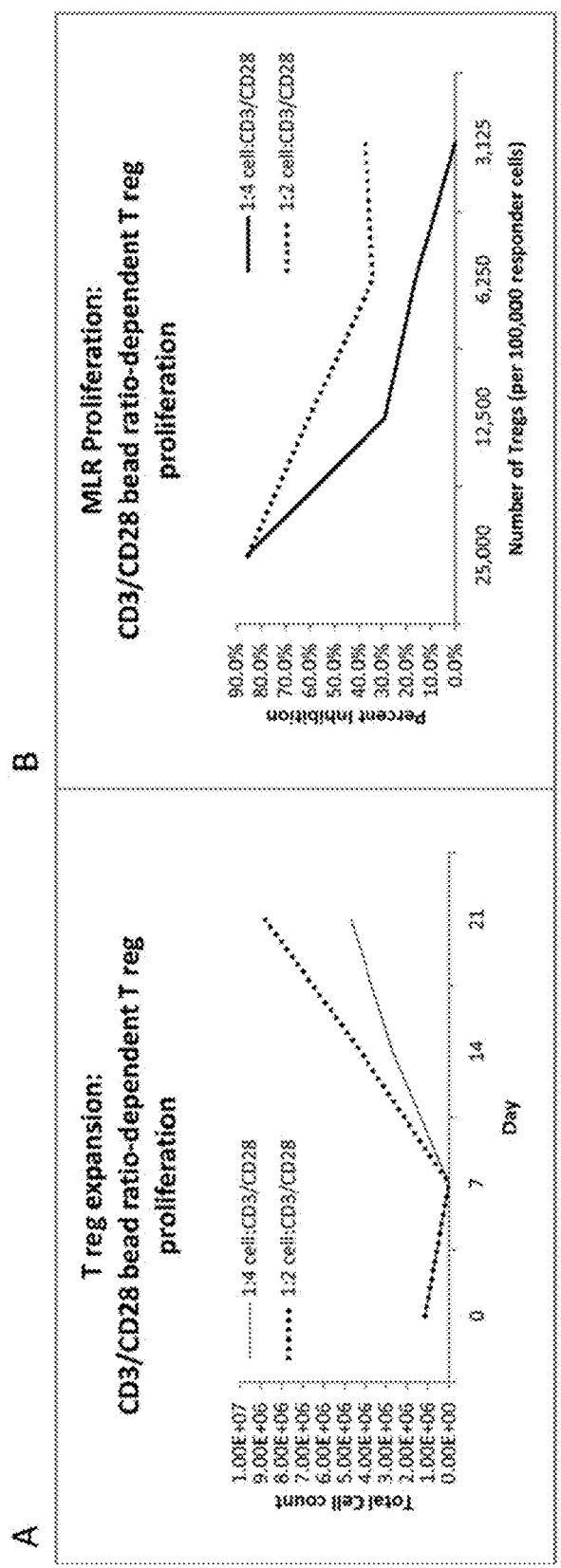
FIG. 7. A. Treg expansion in 1:4 cell to bead ratio of PD-L1-Epoxy bead with 1:2 vs 1:4 cell to bead ratio of CD3/CD28 beads, cultured in 100 ng/ml Rapamycin. B. MLR inhibition potential of Tregs cultured in 1:2 vs 1:4 cell to CD3/CD28 bead ratio.

A schematic of the culture protocol is illustrated in FIG. 5. The following culture conditions were optimized for most effective Treg expansion: (a) Tregs isolated from normal (research) or patient (clinical trial) leukopheresis product were isolated using Milteny CliniMACS Magnetic Cell Separation for Tregs (CD4+, CD25+); (b) Treg cells were cultured in complete medium supplemented with recombinant IL-2, TGF-B and Rapamycin; (c) Cultures will be supplemented with rIL-2 every other day; (d) Rapamycin (100 ng/ml) was added for the first 14 days of culture to inhibit outgrowth of T effector cells and to promote the expansion of Tregs; (e) Stimulation beads were added on day 0 and day 7 of culture: (i) Stimulation with clinical dose of 1:4 cell to bead ratio results in reduced viability of cells and delayed expansion in comparison to 1:2 cell to bead ratio, without effecting the Treg phenotype and functional capacity to inhibit MLR assay; (see FIGS. 5 and 7A and B); (ii) CD3/CD28 beads were added at a 1:2 cell to bead ratio, and PD-L1-beads were added at a 1:2 cell to bead ratio. As illustrated in FIG. 6A, Tregs were expanded using a 1:1, 1:2, or 1:4 cell to bead ratio of PD-L1 bead with 1:2 cell to bead ratio of CD3/CD28 beads in 100 ng/ml Rapamycin. Inhibition in a mixed lymphocyte reaction (MLR) assay was observed for the Tregs cultured as such. (See FIG. 6B). Tregs cultured at a 1:2 cell to bead ratio demonstrated the best inhibition in the MLR assay.

REFERENCES

1. Riella L V, Paterson A M, Sharpe A H, Chandraker; "A Role of the PD-1 Pathway in the Immune Response AJT 2012 12:2575-2587.
2. Francisco L M, Sage P T, and Sharpe A H; "The PD-1 Pathway in Tolerance and Autoimmunity. Immunol Rev 201 236:219-242.
3. Francisco L M, Salinas V H, Brown K E, et al; "PD-L1 Regulates the Development, Maintenance, and Function of Induced Regulatory T Cells. JEM 2009; 206:3015-3029.

Experimental Methods

Coupling of a Recombinant Human PD-L1 Chimera to a Magnetic Bead Support.

A general procedure for coupling antibodies to Dynabeads® M-450 Tosyl-activated magnetic beads (Invitrogen, Catalog No. 14013) or Dynabeads® M-450 Epoxy magnetic beads (Invitrogen, Catalog No. 14011) may be modified in order to similarly couple a PD-L1 Fc chimera (Recombinant Human B7-H1/PD-L1 Fc Chimera, R&D Systems, Catalog Number: 156-B7). The procedure is outlined as follows for both Tosyl-activated and Epoxy: 1. Vortex vial of Dynabeads for heterogeneous distribution for 30 sec; 2. Determine minimum volume required for using sterile flow tubes (200 ul); 3. Take 800 ul of beads ($3.2 \times 10^8$ beads) into a sterile flow tube; 4. Place 200 µl in each flow tube for 4 experimental conditions; 5. Add equal amount of sodium phosphate buffer as beads; 6. Add 200 µl of sodium phosphate buffer (0.1 M, pH 7.6) into each tube; 7. Place in magnet for 1 min and discard the supernatant by tilting the magnet and tubes; 8. Resuspend in 1000 µl of sodium phosphate buffer; 9. Place in magnet for 1 min and discard the supernatant by tilting the magnet and tubes; 10. Resuspend in 560 µl of sodium phosphate buffer; 11. Aliquot 140 µl of Dynabeads per sample into 4 sterile flow tubes; 12. Add protein at concentrations of 100-300 µg/$4 \times 10^8$ beads; this corresponds to 20 µg-60 µg of protein per 140 µl of dynabeads ($0.8 \times 10^8$ beads); 13. Incubate for 15 min at RT standing; 14. Add BSA to 0.01-0.1% w/v; and 15. Incubate overnight at RT by tilting.

For Tosyl-activated beads proceed as follows: 1. Place samples in magnet and discard supenatant; 2. Add 1 ml of PBS buffer (0.1% BSA, 2 mM EDTA, $Ca^{2+}/Mg^{2+}$-free); 3. Incubate 4-8° C. for 5 min by tilting; 4. Apply to magnet and discard supernatant; 5. Add 1 ml of PBS buffer; 6. Incubate 4-8° C. for 5 min by tilting; 7. Add 200 µl of Tris buffer (0.2 M, 0.1% BSA); 8. Incubate 37° C. for 4 hrs by tilting; 9. Apply to magnet and discard supernatant; 10. Add 1 ml of PBS buffer; incubate 4-8° C. for 5 min by tilting; 11. Apply to magnet and discard supernatant; and 12. Resuspend beads in 200 µl of PBS buffer at a concentration of 4×20 beads/ml.

For Epoxy dynabeads proceed as follows: 1. Place samples in magnet and discard supernatant; 2. Add 1 ml of PBS buffer; incubate 4-8° C. for 5 min by tilting; 3. Apply to magnet and discard supernatant; 4. Add 1 ml of PBS; incubate 4-8° C. for 5 min by tilting; 5. Apply to magnet and discard supernatant, and 6. Resuspend beads in 200 µl of PBS buffer at a concentration of $4 \times 20^8$ beads/ml.

Bead saturation may be determined by flowcytometry as follows: 1. Take 2 µl of conjugated beads (2 µl=$8 \times 10^5$ beads) for staining with anti-PD-L1-PE antibody or isotype control; 2. Add 5 µl PE conjugated antibody per 100 µl of analyte; 3. Incubate 4° C. for 15 min; 4. Wash beads with 1 ml Flow Buffer (0.5% BSA, 2 mM EDTA, $Ca^{2+}/Mg^{2+}$-free); 5. Apply to magnet and discard supernatant; 6. Wash beads with 1 ml Flow Buffer; 7. Apply to magnet and discard supernatant; 8. Re-suspend in 200 µl of Flow Buffer; 9. Acquire data using a cytometer; and 10. Optimal saturation of beads is >95% PD-L1-PE$^+$.

Cultivation, Expansion, and Isolation of Human Tregs.

A population of human Tregs may be obtained and tested by the general procedure as follows: (A) Isolation of Peripheral Blood Mononuclear Cells (PBMC) from blood→(B) Isolation of Treg from PBMCs→(C) Culture of Tregs→(D) Functional Assays to Assess Activity of Tregs.

Pre-clinical-grade PBMC may be obtained by the following scheme: 1. Prepare 50 ml centrifuge tubes for layering your blood sample and place 15 ml of lymphocyte separation medium into 50 ml; 2. Mix 100 ml of blood sample with 100 ml of RPMI (at RT) using 15-20 tubes of blood; 3. Slowly layer up to 30 ml of the blood mixture over the 15 ml of lymphocyte separation medium; 4. Spin samples at RT, 2000 RPM, no break, slow acceleration, for 30 min; 5. Remove samples from the centrifuge slowly so as not to disturb the middle layer containing the MNC; 6. Remove most of the top layer but leave ~5 ml of the top layer in order not to disturb the MNC in the middle layer; 7. Collect the middle cloudy layer by swirling gently while pipetting off and avoid taking any of the red layer on the bottom of the tube; 8. Transfer the collected layer to a new tube and pool samples into equal volumes for washing; 9. Spin at 1700 RPM, with full break for 10 min at RT. 10. Decant or aspirate majority of the volume; 11. Pool samples into 1 tube by resuspending in 10 ml RPMI and count cells; and 12. Spin cells at 1200 RPMI, with full break for 10 min at RT. Clinical-grade PBMC from leukopheresis product: 1. Dilute leukopheresis product to a maximum volume of 450 mL in mixing buffer; 2. Centrifuge diluted cells at 800×g (1800 RPM for 15 min at RT; 3. Remove platelets from leukopheresis product using plasma extractor and electronic scale; 4. Leave a volume of 855 mL for CD8+ and CD19+ cell-depletion.

Tregs may be isolated from the PBMCs thus obtained by depleting the PBMC of CD8+ cells and CD19+ cells using CD8 Microbeads and CD19+ Microbeads, respectively (Miltenyi Biotech); and by selecting positively CD25 cells using CD25 Microbeads II (Miltenyi Biotech), according to the following scheme: 1. Incubate the PBMC with anti-human antibodies against CD8 and CD19+ (e.g., Miltenyi 130-045-201 and Miltenyi 130-050-301, Miltenyi Biotech); 2. Deplete the PMBC of CD8+ and CD19+ cells using a LD column (Miltenyi Biotech); Incubate the flow through cells with MicroBeads conjugated to monoclonal anti-CD25 antibody (Miltenyi 130-092-983, Miltenyi Biotech); 3. Select for CD25+ cells using a LS column (Miltenyi Biotech).

Tregs may be cultured using ExpACT Treg Kit (Miltenyi Catalog No. 130-020-007) according to the manufacturer's recommendations either alone ("CD3/CD28 beads only") or with PD-L1 magnetic beads ("CD3/CD28 beads+PD-L1 beads") according to the following scheme: 1. Obtain between 3-4×10⁶ Tregs; 2. Separate the samples into two experimental; groups 1.5-2×10⁶ cells each: (a) Cells+CD3/CD28 beads and (b) Cells+CD3/CD28 beads+PD-L1 Beads; 3. Culture cells in medium above at 1×10⁶ cells/ml; 4. Add beads at a ratio of 1:2 (Tcell:beads) for sample containing CD3/CD28 beads and at a ratio of 1:1 for sample containing PD-L1 beads; 5. On day 1 of culture perform ½ media exchange; 6. On day 7 add fresh CD3/CD28 beads and PD-L1 beads and perform ½ media exchange; 7. On day 14, eliminate Rapamycin from culture by changing medium and immunotype samples for amount of Tregs in cultures; and 8. On day 21, immunotype samples for amount of Tregs in cultures and set up functional assays including a suppression assay and recruitment assay.

A suppression assay may be performed as follows: 1. On day 21 of the Treg culture/expansion, an autologous mixed lymphocyte reaction (MLR) assay may be prepared by combining (a) 100,000 responder PBMC, (b) 100,000 allogeneic irradiated stimulator PMBC; and (c) serial dilutions of 50,000 cultured/expanded Tregs and cultured for 7 days; 2. Add ³H-thymidine; 3. After 24 hrs, harvest cells and measure proliferation by ³H-thymidine incorporation; and 4. Calculate suppression based on inhibition of incorporation of ³H-thymidine by Treg.

A recruitment assay may be performed as follows: 1. On day 21 of the Treg culture/expansion, an autologous mixed lymphocyte reaction (MLR) assay may be performed by combining (a) 50,000 CFSE labeled responder PBMC, (b) 50,000 allogeneic irradiated stimulator PBMC, and (c) serial dilutions of 25,000 PKH-26 labeled, cultured/expanded Tregs; and (2) On day 7, perform flow cytometric analysis of CD4+ and CD8+ subsets and FoxP3 expression.

Example 2—Expansion and Testing of Tregs from Donor #1

Tregs were obtained from a healthy donor under the following protocol and tested accordingly. At day 0, 4.5×10⁸ cells were obtained from freshly isolated PBMC. After depletion of CD8+ and CD19+ cells, 93×10⁶ cells remained. After positive selection for CD25³ cells, 4×10⁶ cells were obtained. These cells were divided into two groups of 2×10⁶ cells. One group was cultured in CD3/CD28 beads. The other group was cultured in CD3/CD28 beads and PD-L1 beads. Both groups were cultured in 100 ng/ml rapamycin, and 500 IU/ml IL-2 per culture medium. On day 1, the culture medium was changed to 100 ng/ml rapamycin, 500 IU/ml IL-2 per culture medium. Every other day thereafter, the culture medium was fed with fresh rapamycin (100 ng/ml) and fresh IL-2 (500 IU/ml). On day 8, fresh CD3/CD28 beads and fresh PD-1 beads were added and culture was continued in 100 nM rapamycin, 500 IU/ml IL-2 per culture medium. Every other day thereafter, the culture medium was fed with fresh rapamycin (100 ng/ml) and fresh IL-2 (500 IU/ml). On day 14, the culture medium was changed to 500 IU/ml IL-2 per culture medium (i.e., removing rapamycin). The following tables illustrate the cell number and % cells exhibiting a given phenotype for the cells grown with CD3/CD28 beads only versus CD3/CD28 beads and PD-L1 beads.

CD3/CD28 Beads Only

| Culture Days | Cell Number ×10⁶ | CD4 Foxp3 % | CD4 CD25 % | CD25 Foxp3 % |
|---|---|---|---|---|
| Day 0 | 2 | 89.2 | | |
| Day 7 | 6.94 | 83.2 | | |
| Day 14 | 13.89 | 75.7 | 87.9 | 75.4 |
| Day 21 | 24 | 81.6 | 88.1 | 81.2 |

CD3/CD28 Beads+PD-L1 Beads

| Culture Days | Cell Number ×10⁶ | CD4 Foxp3 % | CD4 CD25 % | CD25 Foxp3 % |
|---|---|---|---|---|
| Day 0 | 2 | 89.2 | | |
| Day 7 | 7.19 | 82.8 | | |
| Day 14 | 12.8 | 81.2 | 91.0 | 80.4 |
| Day 21 | 21 | 80.8 | 36.1 | 79.6 |

Figure 8:
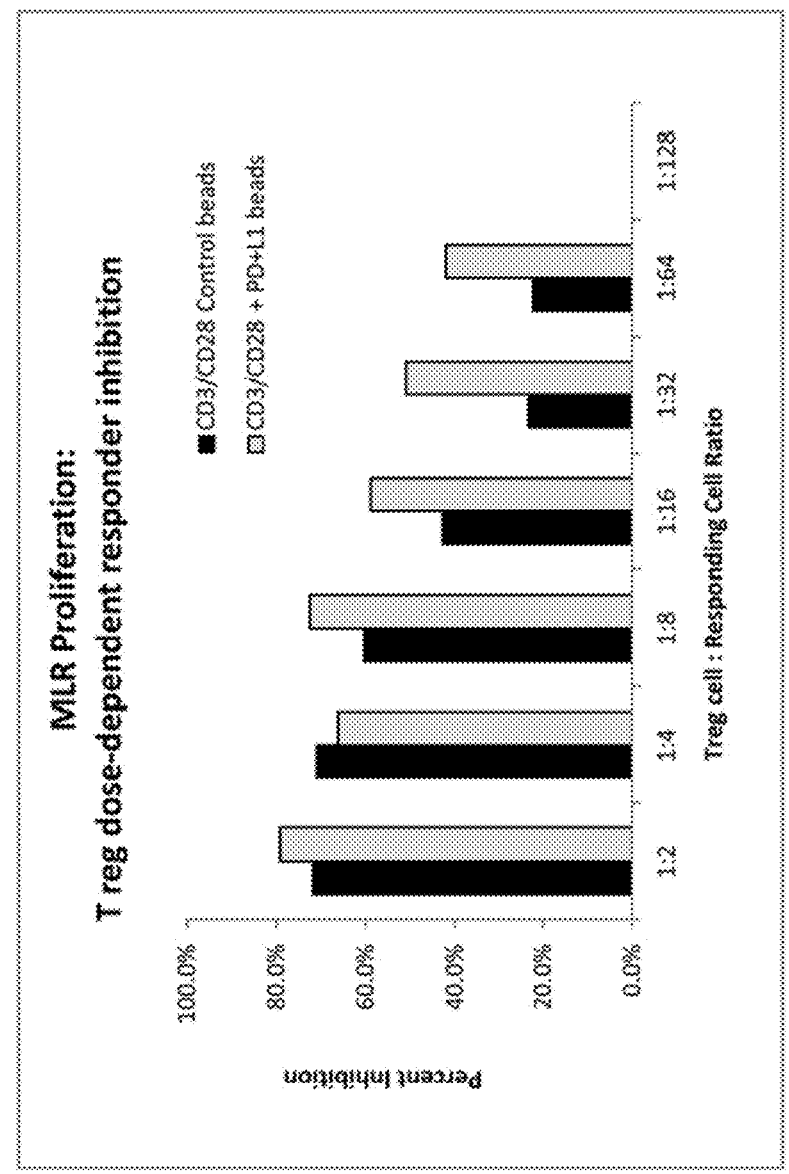
FIG. 8. Suppression assay of Tregs cultured in CD3/CD28 beads versus Tregs cultured in CD3/CD28 beads+PD-L1 beads.

After 21 days, the cells cultured with CD3/CD28 beads and the cells cultured with CD3/CD28 beads+PD-L1 beads were tested in a MLR suppression assay. The results are illustrated in FIG. 8.

Example 3—Expansion and Testing of Tregs from Donor #2

Tregs were obtained from a healthy donor under the following protocol and tested accordingly. At day 0, 3×10⁸ cells were obtained from freshly isolated PBMC. After depletion of CD8+ and CD19+ cells, and after positive selection for CD25+ cells, 4×10⁶ cells were obtained. These cells were divided into two groups of 1.7×10⁶ cells. One group was cultured in CD3/CD28 beads. The other group was cultured in CD3/CD28 beads and PD-L1 beads. Both groups were cultured in 100 nM rapamycin, and 500 IU/ml IL-2 per culture medium. On day 1, fresh culture medium including 100 nM rapamycin, 500 IU/ml IL-2 was added. Every other day thereafter, the culture medium was fed with fresh rapamycin (100 nM) and fresh IL-2 (500 IU/ml). On day 8, fresh CD3/CD28 beads and fresh PD-L1 beads were added and culture was continued in 100 nM rapamycin, 500 IU/ml IL-2 per culture medium. Every other day thereafter, the culture medium was fed with fresh rapamycin (100 nM) and fresh IL-2 (500 IU/ml). On day 14, the culture medium was changed to 500 IU/ml IL-2 per culture medium (i.e., removing rapamycin). The following tables illustrate the cell number and % cells exhibiting a given phenotype for the cells grown with CD3/CD28 beads only versus CD3/CD28 beads and PD-L1 beads.

CD3/CD28 Beads Only

| Culture Days | Cell Number ×10$^6$ | CD4 Foxp3 % | CD4 CD25 % | CD25 Foxp3 % |
|---|---|---|---|---|
| Day 0 | 1.7 | 85.4 | | |
| Day 7 | 7.7 | | | |
| Day 14 | 15.1 | 63.3 | 65.3 | |
| Day 21 | 10 | 92.0 | 93.0 | 86.0 |

CD3/CD28 Beads+PD-L1 Beads

| Culture Days | Cell Number ×10$^6$ | CD4 Foxp3 % | CD4 CD25 % | CD25 Foxp3 % |
|---|---|---|---|---|
| Day 0 | 1.7 | 85.4 | | |
| Day 7 | 8.7 | | | |
| Day 14 | 12.4 | 65.1 | 68.3 | |
| Day 21 | 8 | 89.4 | 89.2 | 85.0 |

Figure 9:
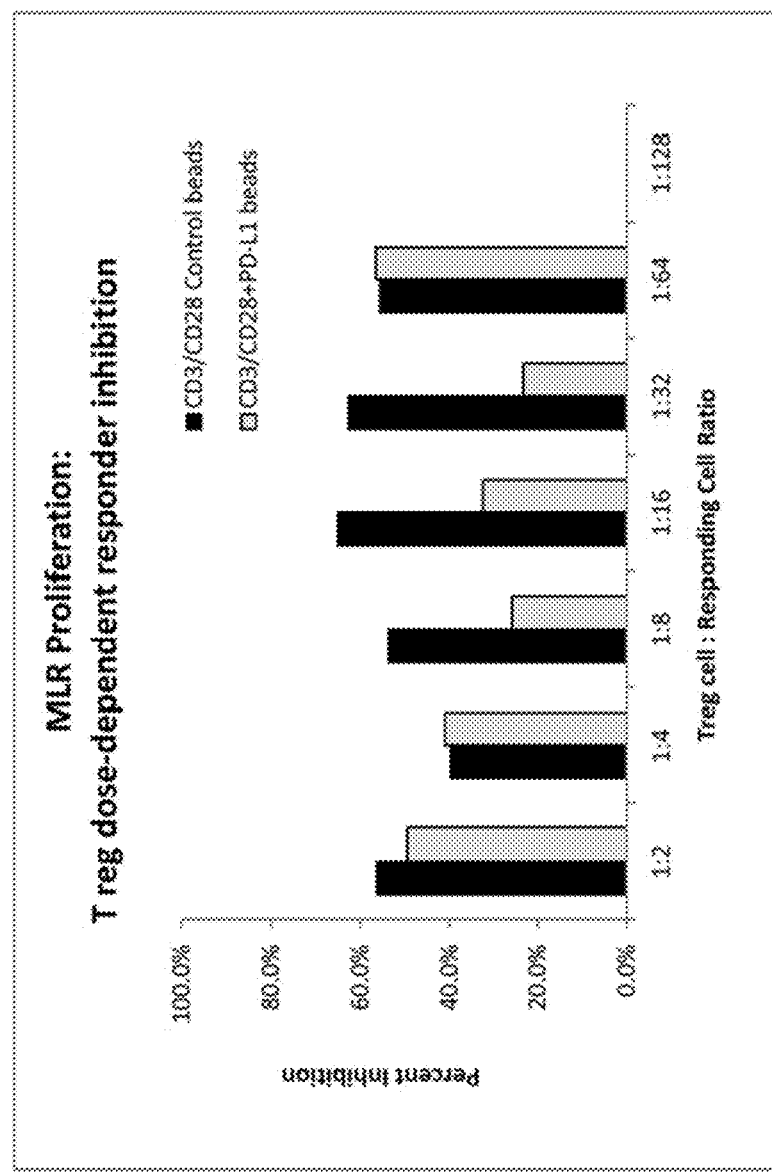
FIG. 9. Suppression assay of Tregs cultured in CD3/CD28 beads versus Tregs cultured in CD3/CD28 beads+PD-L1 beads.

After 21 days, the cells cultured with CD3/CD28 beads and the cells cultured with CD3/CD28 beads+PD-L1 beads were tested in a MLR suppression assay. The results are illustrated in FIG. 9.

Example 4—Further Testing of Tregs

Figure 10:
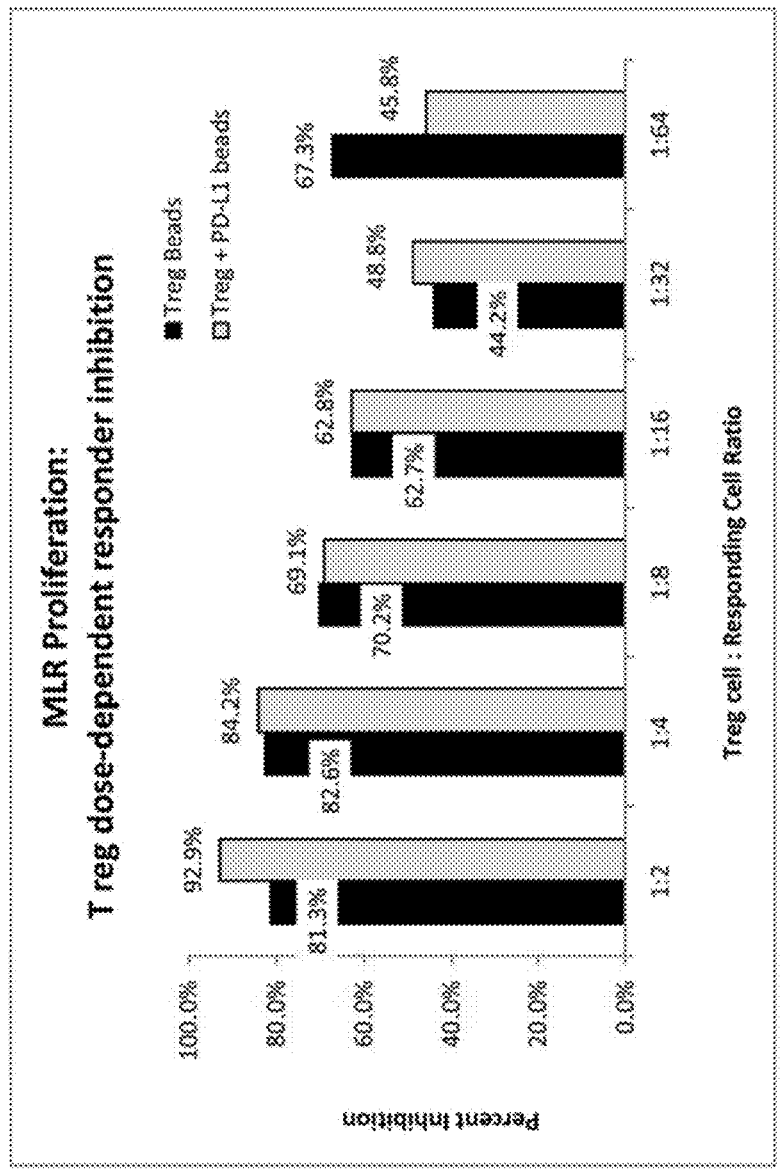
FIG. 10. Suppression assay of Tregs cultured in CD3/CD28 beads versus Tregs cultured in CD3/CD28 beads+PD-L1 beads.
Figure 11:
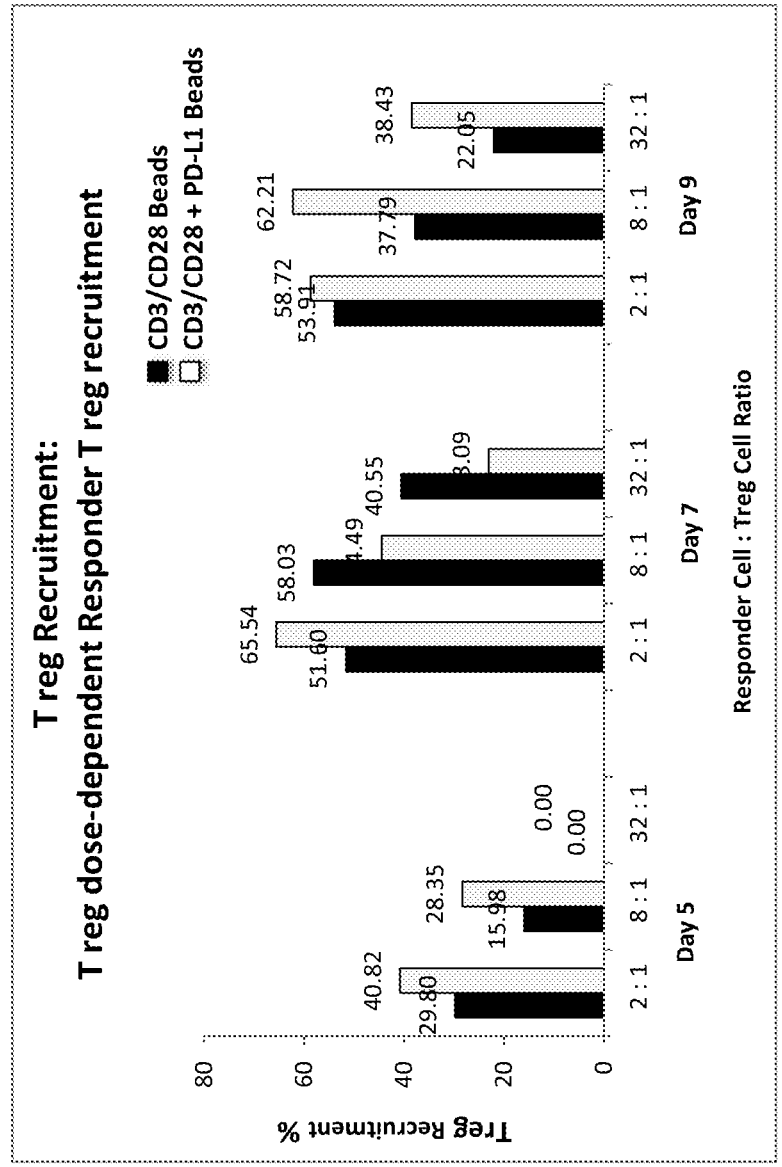
FIG. 11. Recruitment assay of Tregs cultured in CD3/CD28 beads versus Tregs cultured in CD3/CD28 beads+PD-L1 beads.

Tregs cultured with CD3/CD28 beads or cultured with CD3/CD28 beads+PD-L1 beads were tested in a suppression assay and a recruitment assay. The results of these assays are provided in FIGS. 10 and 11, respectively.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

We claim:

1. A method for cultivating a population of T cells comprising regulatory T cells (Tregs), the method comprising cultivating the population of T cells in a culture media comprising a ligand that activates the programmed cell death receptor (PD-1) conjugated to a solid support, wherein prior to cultivating the population of T cells, greater than about 80% of the population of T cells have a phenotype of CD4$^+$, CD25$^+$, CD127$^{low}$ and greater than about 60% of the population of T cells have a phenotype of Foxp3$^+$, and wherein after cultivating the population of T cells, greater than about 80% of the population of T cells have a phenotype of CD4$^+$, CD25$^+$, CD127$^{low}$ and greater than about 60% of the population of T cells have a phenotype of Foxp3$^+$.

2. The method of claim 1, wherein the ligand is PD-L1 protein and the solid support is a magnetic or paramagnetic bead.

3. The method of claim 1, wherein the population of T cells comprises Tregs isolated from peripheral blood mononuclear cells (PBMCs).

4. The method of claim 3 wherein the Tregs are isolated from the PBMCs by removing cells that are CD8$^+$ and CD19$^+$ from the PMBCs and by selecting for cells that are CD25$^+$ in the PMBCs.

5. The method of claim 1, wherein the culture media further comprises an antibody against CD3 conjugated to a solid support.

6. The method of claim 5, wherein the solid support is a magnetic or paramagnetic bead.

7. The method of claim 1, wherein the culture media further comprises a cytokine.

8. The method of claim 7, wherein the cytokine is IL-2.

9. The method of claim 1, wherein the culture media further comprises rapamycin.

10. The method of claim 1, wherein the culture media further comprises a growth factor.

11. The method of claim 10, wherein the growth factor is TGF-beta.

12. The method of claim 1, wherein the population of T cells is cultivated for at least 7 days.

13. A method for cultivating a population of T cells comprising regulatory T cells (Tregs), the method comprising cultivating the population of T cells in a culture media comprising a ligand that activates the programmed cell death receptor (PD-1) conjugated to a solid support, wherein prior to cultivating the population of T cells, greater than about 80% of the population of T cells have a phenotype of CD4$^+$, CD25$^+$, CD127$^{low}$ and greater than about 60% of the population of T cells have a phenotype of Foxp3$^+$, and wherein after cultivating the population of T cells, greater than about 80% of the population of T cells have a phenotype of $CD4^+$, $CD25^+$, $CD127^{low}$ and greater than about 60% of the population of T cells have a phenotype of $Foxp3^+$, wherein the ligand is PD-L1 protein and the solid support is a magnetic or paramagnetic bead and wherein prior to cultivating the population of T cells, the culture media has a ratio of T cells to beads of 1:(1-4).

14. The method of claim 13, wherein the population of T cells comprises Tregs isolated from peripheral blood mononuclear cells (PBMCs) and the Tregs are isolated from the PBMCs by removing cells that are $CD8^+$ and $CD19^+$ from the PMBCs and by selecting for cells that are $CD25^+$ in the PMBCs.

15. The method of claim 13, wherein the culture media further comprises an antibody against CD3 conjugated to a solid support and the solid support is a magnetic or paramagnetic bead.

16. The method of claim 13, wherein the culture media further comprises IL-2.

17. The method of claim 13, wherein the culture media further comprises TGF-beta.

18. The method of claim 13, wherein the population of T cells is cultivated for at least 7 days.

19. A method for cultivating a population of T cells comprising regulatory T cells (Tregs), the method comprising cultivating the population of T cells in a culture media comprising a ligand that activates the programmed cell death receptor (PD-1) conjugated to a solid support, wherein prior to cultivating the population of T cells, greater than about 80% of the population of T cells have a phenotype of $CD4^+$, $CD25^+$, $CD127^{low}$ and greater than about 60% of the population of T cells have a phenotype of $Foxp3^+$, and wherein after cultivating the population of T cells, greater than about 80% of the population of T cells have a phenotype of $CD4^+$, $CD25^+$, $CD127^{low}$ and greater than about 60% of the population of T cells have a phenotype of $Foxp3^+$, wherein the ligand is a PD-L1-Fc chimera protein and the solid support is magnetic or paramagnetic beads and the magnetic or paramagnetic beads have a concentration of ligand of 25-75 µg ligand per $1\times10^8$ beads.

20. The method of claim 19, wherein the population of T cells is cultivated for at least 7 days.

* * * * *